US007375226B2

(12) United States Patent
Jolidon et al.

(10) Patent No.: US 7,375,226 B2
(45) Date of Patent: May 20, 2008

(54) BI- AND TRICYCLIC SUBSTITUTED PHENYL METHANONES

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/297,597

(22) Filed: Dec. 8, 2005

(65) Prior Publication Data
US 2006/0128713 A1 Jun. 15, 2006

(30) Foreign Application Priority Data
Dec. 15, 2004 (EP) ................... 04106597

(51) Int. Cl.
C07D 495/04 (2006.01)
A61K 31/4365 (2006.01)
(52) U.S. Cl. .................... 546/80; 514/232.8; 514/291; 544/126
(58) Field of Classification Search ............... 546/80, 546/186
See application file for complete search history.

(56) References Cited

U.S. PATENT DOCUMENTS

| 3,933,802 | A | 1/1976 | Ferrini et al. |
| 4,244,871 | A | 1/1981 | Kosary et al. |
| 6,001,854 | A | 12/1999 | Ognyanov et al. |
| 2004/0023947 | A1* | 2/2004 | Martin et al. ............. 514/215 |
| 2005/0059668 | A1 | 3/2005 | Alberati-Giani et al. |
| 2005/0070539 | A1 | 3/2005 | Alberati-Giani et al. |
| 2005/0209241 | A1 | 9/2005 | Jolidon et al. |

FOREIGN PATENT DOCUMENTS

| EP | 0 171 636 | 2/1985 |
| EP | 0 624 584 | 11/1994 |
| WO | WO 99/44596 | 9/1999 |
| WO | WO 99/45011 | 9/1999 |
| WO | WO 01/81308 A2 | 11/2001 |
| WO | WO 02/22612 | 3/2002 |
| WO | WO 03/004480 | 1/2003 |
| WO | WO 03/035602 | 5/2003 |
| WO | WO 2004/037800 | 5/2004 |
| WO | WO 2005/023260 A1 | 3/2005 |
| WO | WO 2005/023261 A1 | 3/2005 |

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148.
Caulfield W. L. et al., Journal of Med. Chem. vol. 44(17) pp. 2679-2682 (2001).
Chem. Abstract XP-002299149.
Chemical Abstracts Service, Apr. 23, 2003, XP002308402, Database accession No. 2003: 2142911 Chemcats & Catalog: AsInExExpress Gold.
Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.
Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.

(Continued)

*Primary Examiner*—Bernard Dentz
*Assistant Examiner*—David E Gallis
(74) *Attorney, Agent, or Firm*—George W. Johnston; Patricia S. Rocha-Tramaloni; Kimberly J. Prior

(57) ABSTRACT

The present invention relates to compounds of formula IA

IA

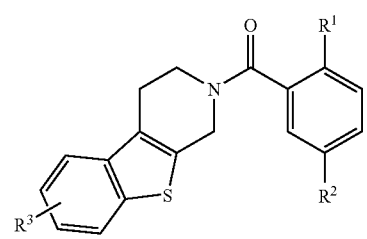

wherein $R^1$, $R^2$, $R^3$, and n are as defined in the specification, and to pharmaceutically active acid addition salts thereof. The compounds of the invention are useful in the treatment of neurological and neuropsychiatric disorders.

8 Claims, No Drawings

OTHER PUBLICATIONS

Chemical Abstracts Service, XP002308978.
Chemical Abstracts Service, XP002308979; Chemcats No. 2003:1026314.
Chemical Abstracts Service, XP002308980; Chemcats No. 2001;2814605.
Chemical Abstracts Service, XP002308981; Chemcats No. 2002:2063001.
Chemical Abstracts Service, XP002308983; Chemcats No. 2003:1026533.
Chemical Abstracts Service, XP002308984; Chemcats No. 2002:2288893.
Chemical Abstracts Service, XP002308985; Chemcats No. 2003:709504.
Chemical Abstracts Service, XP002308986; Chemcats No. 2003:709503.
Chemical Abstracts Service, XP002308987; Chemcats No. 2003:709505.
Chemical Abstracts Service, XP002308988; Chemcats No. 2004:1498769.
Chemical Abstracts Service, XP002308989; Chemcats No. 2002:2386068.
Chemical Abstracts Service, XP002308990; Chemcats No. 2002:2894607.
Chemical Abstracts Service, XP002308991; Chemcats No. 2003:3342164.
Chemical Abstracts Service, XP002308992; Chemcats No. 2003:3345505.
Chemical Abstracts Service, XP002308993; Chemcats No. 2003:3346187.
Chemical Abstracts Service, XP002309007; Chemcats No. 2004:660630.
Abstract corresponding to Document B5—WO 03/035602.
Derwent Publication, XP002370375 & JP 08 325234.

* cited by examiner

BI- AND TRICYCLIC SUBSTITUTED PHENYL METHANONES

PRIORITY TO RELATED APPLICATIONS

This application claims the benefit of European Application No. 04106597.0, filed Dec. 15, 2004, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D. A. and Lieberman J. A., Neuron, 2000, 28:325-33). For decades research has focused on the "dopaminergic hyperactivity" hypothesis which has led to therapeutic interventions involving blockade of the dopaminergic system (Vandenberg R. J. and Aubrey K. R., Exp. Opin. Ther. Targets, 2001, 5(4):507-518; Nakazato A. and Okuyama S., et al., 2000, Exp. Opin. Ther. Patents, 10(1):75-98). This pharmacological approach poorly address negative and cognitive symptoms which are the best predictors of functional outcome (Sharma, T., Br. J. Psychiatry, 1999, 174 (Suppl. 28): 44-51)).

A complementary model of schizophrenia was proposed in the mid-1960's based upon the psychotomimetic action caused by the blockade of the glutamate system by compounds like phencyclidine (PCP) and related agents (ketamine) which are non-competitive NMDA receptor antagonists. Interestingly in health volunteers, PCP-induced psychotomimetic action incorporates positive and negative symptoms as well as cognitive dysfunction, thus closely resembling schizophrenia in patients (Javitt D. C. et al., 1999, Biol. Psychiatry, 45:668-679 and refs. herein). Furthermore, transgenic mice expressing reduced levels of the NMDARI subunit displays behavioural abnormalities similar to those observed in pharmacologically induced models of schizophrenia, supporting a model in which reduced NMDA receptor activity results in schizophrenia-like behavior (Mohn, A. R. et al., 1999, Cell, 98:427-436).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb, D. O., 1949, The Organization of Behavior, Wiley, N.Y.; Bliss T. V. and Collingridge G. L., 1993, Nature, 361:31-39). Transgenic mice over expressing the NMDA NR2B subunit exhibit enhanced synaptic plasticity and superior ability in learning and memory (Tang, J. P. et al., 1999, Nature, Vol. 401, pgs. 63-69).

Thus, if a glutamate deficit is implicated in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R. R. et al., 2002, Trends in Pharm, Sci., 23(8):367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B. et al., 2001, Mol. Mem. Biol., 18:13-20). Thus, one strategy to enhance NMDA receptor activity is to evaluate the glycine concentration in the local microenvironment of synaptic NMDA receptors by inhibition of GlyT-1 transporter (Bergeron R. et al., 1998, Proc. Natl. Acad. Sci. USA, 95:15730-15734; Chen L. et al., 2003, J. Neurophysiol., 89(2):691-703). Glycine transporters inhibitors are suitable for the treatment of neurological and neuropsychiatric disorders. The majority of diseases states implicated are psychoses, schizophrenia (Armer R. E. and Miller D. J., 2001, Exp. Opin. Ther. Patents, 11(4):563-572), psychotic mood disorders such as severe major depressive disorder, mood disorders associated with psychotic disorders such as acute mania or depression associated with bipolar disorders and mood disorders associated with schizophrenia, (Pralong, E. T. et al., 2002, Prog. Neurobiol., 67:173-202), autistic disorders (Carlsson M. L. 1998, J. Neural. Transm. 105:525-535), cognitive disorders such as dementias, including age related dementia and senile dementia of the Alzheimer type, memory disorders in a mammal, including a human, attention deficit disorders and pain (Armer R. E. and Miller D. J., 2001, Exp. Opin. Ther. Patents 11(4):563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of the formula I

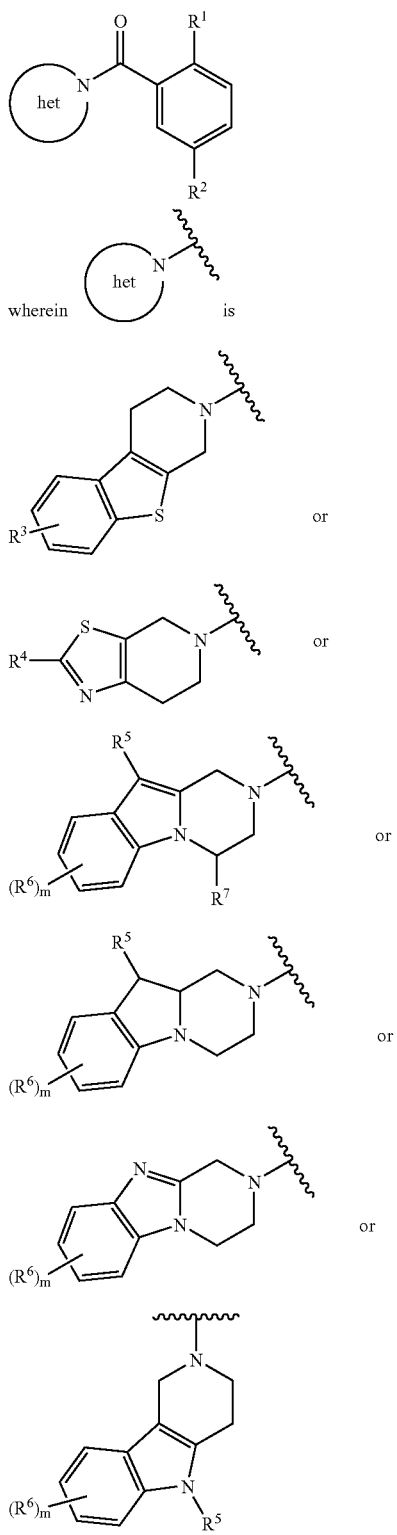

wherein het is

A, B, C, D, E, or F

R¹ is a non aromatic heterocycle, OR' or N(R")₂;
R' is lower alkyl, lower alkyl substituted by halogen or —(CH₂)ₙ-cycloalkyl;
R" is lower alkyl;
R² is NO₂, CN or SO₂R";
R³ is hydrogen, halogen, lower alkyl, lower alkoxy, or lower alkyl substituted by halogen;
R⁴ is hydrogen, lower alkyl, phenyl substituted by halogen or CF₃, or is a five or six membered aromatic heterocycle;
R⁵ and R⁶ are each independently hydrogen, halogen, lower alkyl, lower alkoxy, lower alkyl substituted by halogen, or lower alkoxy substituted by halogen;
R⁷ is hydrogen or lower alkyl;
m is 1 or 2; and
n is 0, 1 or 2;

and pharmaceutically active acid addition salts thereof.

Furthermore, the invention includes all racemic mixtures, all their corresponding enantiomers and/or optical isomers. The present invention also provides processes for preparation of such compounds and pharmaceutical compositions containing them.

Compounds of formula I are good inhibitors of the glyicne transporter 1 (GlyT-1), and have good selectivity to glycine transporter 2 (GlyT-2) inhibitors. Therefore, these compounds are useful for the treatment of diseases related to activation of NMDA receptors via GlyT-1 inhibition. The present invention provides methods for treating neurological and neuropsychiatric disorders such as psychoses, dysfunction in memory and learning, schizophrenia, dementia and other diseases in which cognitive processes are impaired, such as attention deficit disorders or Alzheimer's disease. The preferred indications of the invention are schizophrenia, cognitive impairment and Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated carbon ring, containing from 3 to 7 carbon atoms, for example, cyclopropyl, cyclopentyl and cyclohexyl.

As used herein the term "non aromatic heterocycle" denotes a five or six membered heterocyclic ring, containing one or two heteroatoms, selected from the group consisting of O, N or S. Preferred rings are 1-pyrrolidine, 1-piperidine, 1-piperazine and 1-morpholine.

The term "five or six membered aromatic heterocycle" denotes an aromatic ring having one, two or three heteroatoms. Examples include furanyl, thiophenyl, pyrrolyl, pyridinyl and the like.

The term "halogen" denotes chlorine, iodine, fluorine and bromine.

As used herein the term "lower alkyl substituted by halogen" denotes an alkyl group as defined above, wherein at least one hydrogen atom is replaced by halogen, for example CF$_3$, CHF$_2$, CH$_2$F, CH(CH$_3$)CF$_3$, CH$_2$CF$_3$ and the like.

The term "lower alkoxy" denotes the residue —O-R, wherein R is a lower alkyl residue as defined herein.

The term "lower alkoxy substituted by halogen" denotes the residue —O-R, wherein R is a lower alkyl group as defined herein and wherein at least one hydrogen atom is replaced by halogen, for example OCF$_3$, OCHF$_2$, OCH$_2$F, OCH(CH$_3$)CF$_3$, OCH$_2$CF$_3$ and the like.

The term "pharmaceutically acceptable" such as pharmaceutically acceptable carrier, excipient, etc., means pharmacologically acceptable and substantially non-toxic to the subject to which the particular compound is administered.

The terms "pharmaceutically acceptable acid addition salts" or "pharmaceutically active acid addition salts" embrace salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

The present invention provides compounds of formula I

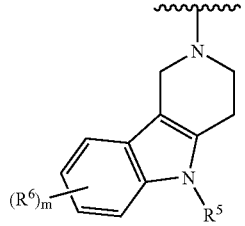

I wherein

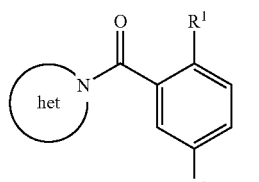 is

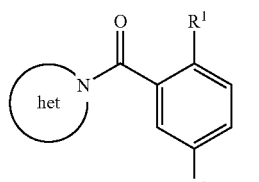

A

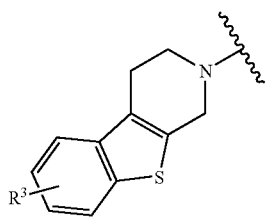 or

B

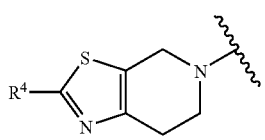 or

C

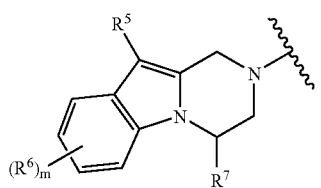 or

-continued

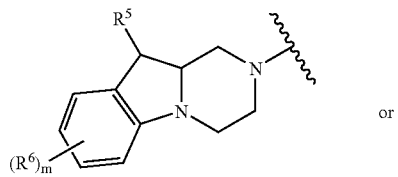 D or

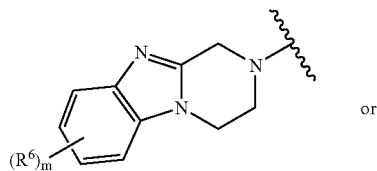 E or

F $R^1$ is a non aromatic heterocycle, OR' or N(R")$_2$;
R' is lower alkyl, lower alkyl, substituted by halogen or —(CH$_2$)$_n$-cycloalkyl;
R" is lower alkyl;
$R^2$ is NO$_2$, CN or SO$_2$R";
$R^3$ is hydrogen, halogen, lower alkyl, lower alkoxy, or lower alkyl substituted by halogen;
$R^4$ is hydrogen, lower alkyl, phenyl substituted by halogen or CF$_3$, or is a five or six membered aromatic heterocycle;
$R^5$ and $R^6$ are each independently hydrogen, halogen, lower alkyl, lower alkoxy, lower alkyl substituted by halogen, or lower alkoxy substituted by halogen;
$R^7$ is hydrogen or lower alkyl;
m is 1 or 2; and
n is 0, 1 or 2;

and pharmaceutically active acid addition salts thereof.

Compounds of formulae IA, IB, IC, ID, IE and IF are encompassed by the present invention.

The invention provides compounds of formula IA

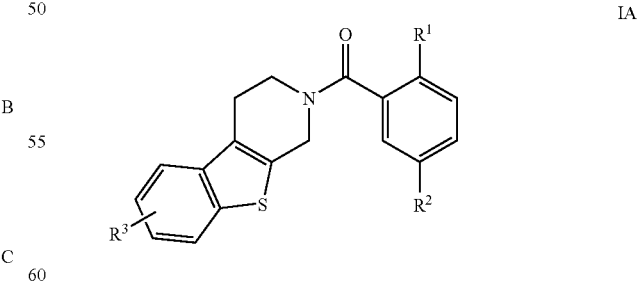

IA wherein
R' is a non aromatic heterocycle, OR' or N(R")$_2$;
R' is lower alkyl, lower alkyl substituted by halogen or —(CH$_2$)$_n$-cycloalkyl;
R" is lower alkyl;
$R^2$ is NO$_2$, CN or SO$_2$R";

R³ is hydrogen, halogen, lower alkyl, lower alkoxy, or lower alkyl substituted by halogen;
n is 0, 1 or 2;
or a pharmaceutically active acid addition salt thereof.

Preferred compounds of formula IA are the following:
(6-Chloro-3,4-dihydro-1H-benzo[4,5]thieno[2,3-c]pyridin-2-yl)-(2-isopropoxy-5-methanesulfonyl-phenyl)-methanone,
(6-Chloro-3,4-dihydro-1H-benzo[4,5]thieno[2,3-c]pyridin-2-yl)-(5-methanesulfonyl-2-morpholin-4-yl-phenyl)-methanone,
3-(6-chloro-3,4-dihydro-1H-benzo[4,5]thieno[2,3-c]pyridine-2-carbonyl)-4-isopropoxy-benzonitrile,
(6-chloro-3,4-dihydro-1H-benzo[4,5]thieno[2,3-c]pyridin-2-yl)-(2-cyclopropylmethoxy-5-methanesulfonyl-phenyl)-methanone and
(6-chloro-3,4-dihydro-1H-benzo[4,5]thieno[2,3-c]pyridin-2-yl)-[5-methanesulfonyl-2-((S)-2,2,2-trifluoro-1-methyl-ethoxy)-phenyl]-methanone.

The invention provides compounds of formula IB

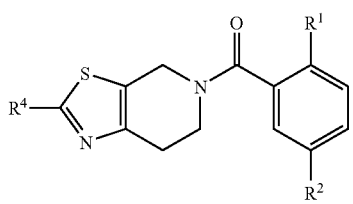

wherein
R¹ is a non aromatic heterocycle, OR' or N(R")₂;
R' is lower alkyl, lower alkyl substituted by halogen or —(CH₂)$_n$-cycloalkyl;
R" is lower alkyl;
R² is NO₂, CN or SO₂R";
R⁴ is hydrogen, lower alkyl phenyl substituted by halogen or CF₃, or is a five or six membered aromatic heterocycle;
n is 0, 1 or 2;
or a pharmaceutically active acid addition salt thereof.

Preferred compounds of formula IB are
(2-isobutoxy-5-methanesulfonyl-phenyl)-(2-thiophen-2-yl-6,7-dihydro-4H-thiazolo[5,4-c]pyridin-5-yl)-methanone,
(2-isopropoxy-5-methanesulfonyl-phenyl)-(2-thiophen-2-yl-6,7-dihydro-4H!-thiazolo[5,4-c]pyridin-5-yl)-methanone and
(2-isobutoxy-5-methanesulfonyl-phenyl)-[2-(4-trifluoromethyl-phenyl)-6,7-dihydro-4H-thiazolo[5,4-c]pyridin-5-yl]-methanone.

The invention provides compounds of formula IC

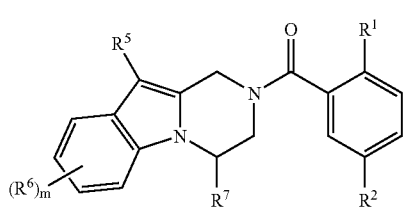

wherein
R¹ is a non aromatic heterocycle, OR' or N(R")₂;
R' is lower alkyl, lower alkyl substituted by halogen or —(CH₂)$_n$-cycloalkyl;
R" is lower alkyl;
R² is NO₂, CN or SO₂R";
R⁵ and R⁶ are each independently hydrogen, halogen, lower alkyl, lower alkoxy, lower alkyl substituted by halogen or lower alkoxy, substituted by halogen;
R⁷ is hydrogen or lower alkyl;
m is 1 or 2; and
n is 0, 1 or 2;
or a pharmaceutically active acid addition salt thereof.

Preferred compounds of formula IC are
(7-chloro-3,4-dihydro-1H-pyrazino[1,2-a]indol-2-yl)-(2-isopropoxy-5-methanesulfonyl-phenyl)-methanone and
(2-isopropoxy-5-methanesulfonyl-phenyl)-(8-trifluoromethoxy-3,4-dihydro-1H-pyrazino[1,2-a]indol-2-yl)-methanone.

The invention provides compounds of formula ID

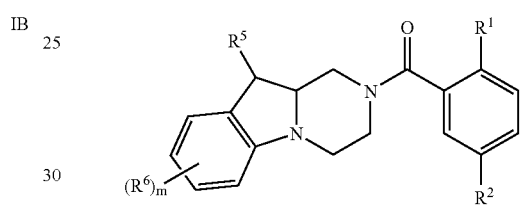

wherein
R¹ is a non aromatic heterocycle, OR' or N(R")₂;
R' is lower alkyl, lower alkyl substituted by halogen or —(CH₂)$_n$-cycloalkyl;
R" is lower alkyl;
R² is NO₂, CN or SO₂R";
R⁵ and R⁶ are each independently hydrogen, halogen, lower alkyl, lower alkoxy, lower alkyl substituted by halogen or lower alkoxy, substituted by halogen;
m is 1 or 2; and
n is 0, 1 or 2;
or a pharmaceutically active acid addition salt thereof.

A preferred compound of formula ID is
Rac-(2-isopropoxy-5-methanesulfonyl-phenyl)-(8-trifluoromethoxy-3,4,10,10a-tetrahydro-1H-pyrazino[1,2-a]indol-2-yl)-methanone.

The invention provides compounds of formula IE

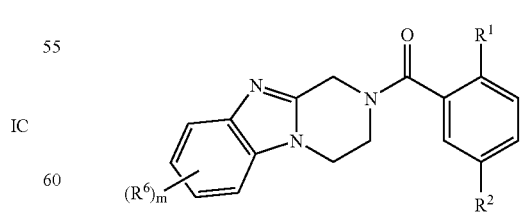

wherein
R¹ is a non aromatic heterocycle, OR' or N(R")₂;
R' is lower alkyl, lower alkyl substituted by halogen or —(CH₂)$_n$-cycloalkyl;

R" is lower alkyl;
R² is NO₂, CN or SO₂R";
R⁶ is hydrogen, halogen, lower alkyl, lower alkoxy, lower alkyl substituted by halogen or lower alkoxy substituted by halogen;
m is 1 or 2; and
n is 0, 1 or 2;

or a pharmaceutically active acid addition salt thereof.

A preferred compound of formula IE is (2-cyclopentyloxy-5-methanesulfonyl-phenyl)-(3,4-dihydro-1H-benzo[4,5]imidazo[1,2-a]pyrazin-2-yl)-methanone.

The invention provides compounds of formula IF

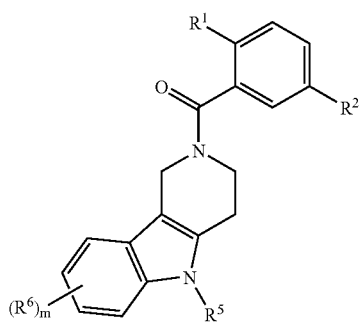

IF wherein
R¹ is a non aromatic heterocycle, OR' or N(R")₂;
R' is lower alkyl, lower alkyl substituted by halogen or —(CH₂)ₙ-cycloalkyl;
R" is lower alkyl;
R² is NO₂, CN or SO₂R";
R⁵ and R⁶ are each independently hydrogen, halogen, lower alkyl, lower alkoxy, lower alkyl substituted by halogen or lower alkoxy substituted by halogen;
m is 1 or 2; and
n is 0, 1 or 2;

or a pharmaceutically active acid addition salt thereof.

Compounds of formula IF are also preferred.

The present compounds of formula I and their pharmaceutically acceptable salts can be prepared by methods known in the art, for example, by processes described below, which process comprises
a) reacting a compound of formula

II selected from the group consisting of

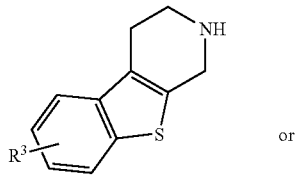

IIA or

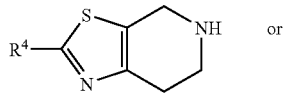

IIB or

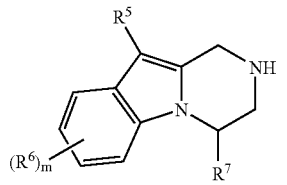

IIC or

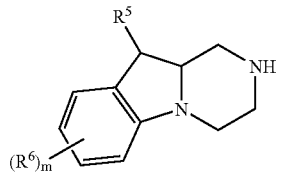

IID or

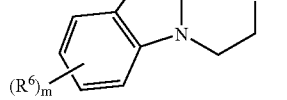

IIE or

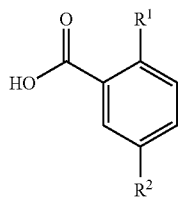

IIF with a compound of formula

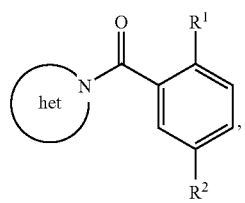

III in the presence of an activating agent, such as TBTU, to produce a compound of formula

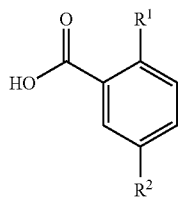

I wherein in dependency of

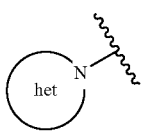

the following structures are encompassed by formula I

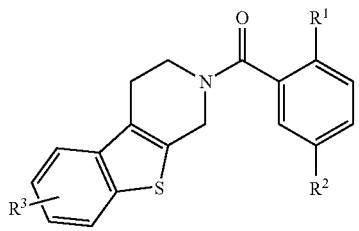
IA or

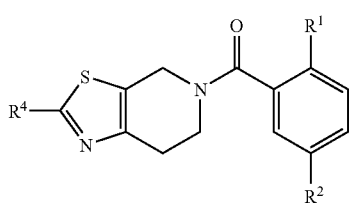
IB or

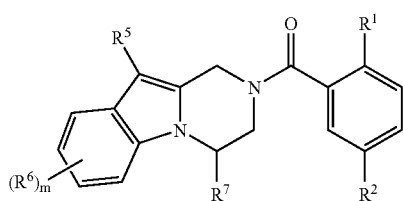
IC or

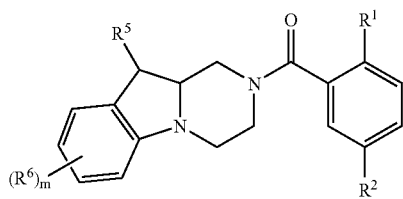
ID or

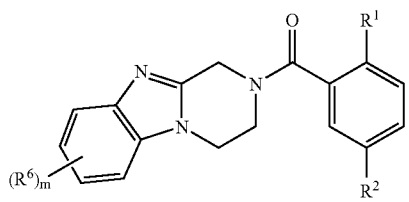
IE or

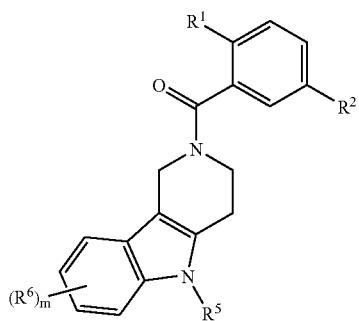
IF wherein the substituents are as defined above, or
b) reacting a compound of formula

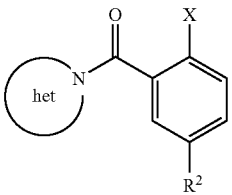
IV with a compound of formula

R¹H      V in the presence of a base, such as triethylamine, or a catalyst like Cu(I)Br, to produce a compound of formula

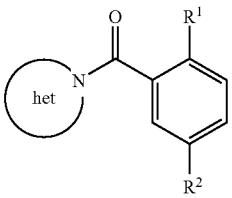
I wherein the substituents $R^1$, $R^2$ and

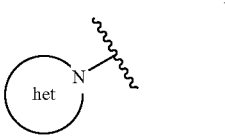

are as defined above, and X is halogen, or
c) reacting a compound of formula

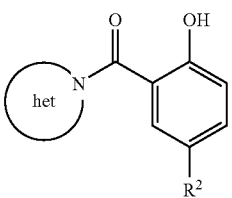
VI with a compound of formula

R'X      VII to produce a compound of formula

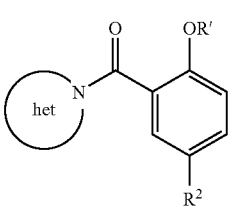
I1 wherein the substituents R², R' and

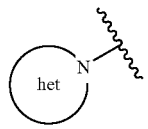

are as defined above and X is halogen, or
d) reacting a compound of formula

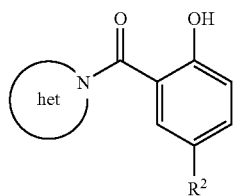

VI with a compound of formula

R'OH    VIII under Mitsunobu conditions to produce a compound of formula

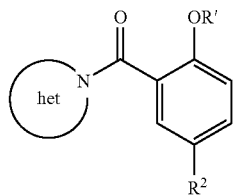

II wherein the substituents R², R' and

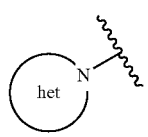

are as defined above, and if desired, converting the compounds obtained into pharmaceutically acceptable acid addition salts.

The compounds of formula I can be prepared in accordance with process variants a), b) c) or d) and with the following schemes 1, 2, 3 and 4. All starting materials are either commercially available, described in the literature or can be prepared by methods well known in the art.

The following abbreviation has been used:
TBTU=(2-(1H-benzotriazole-1-yl)-1,1,3,3-tetramethyluroniumtetrafluoroborate)

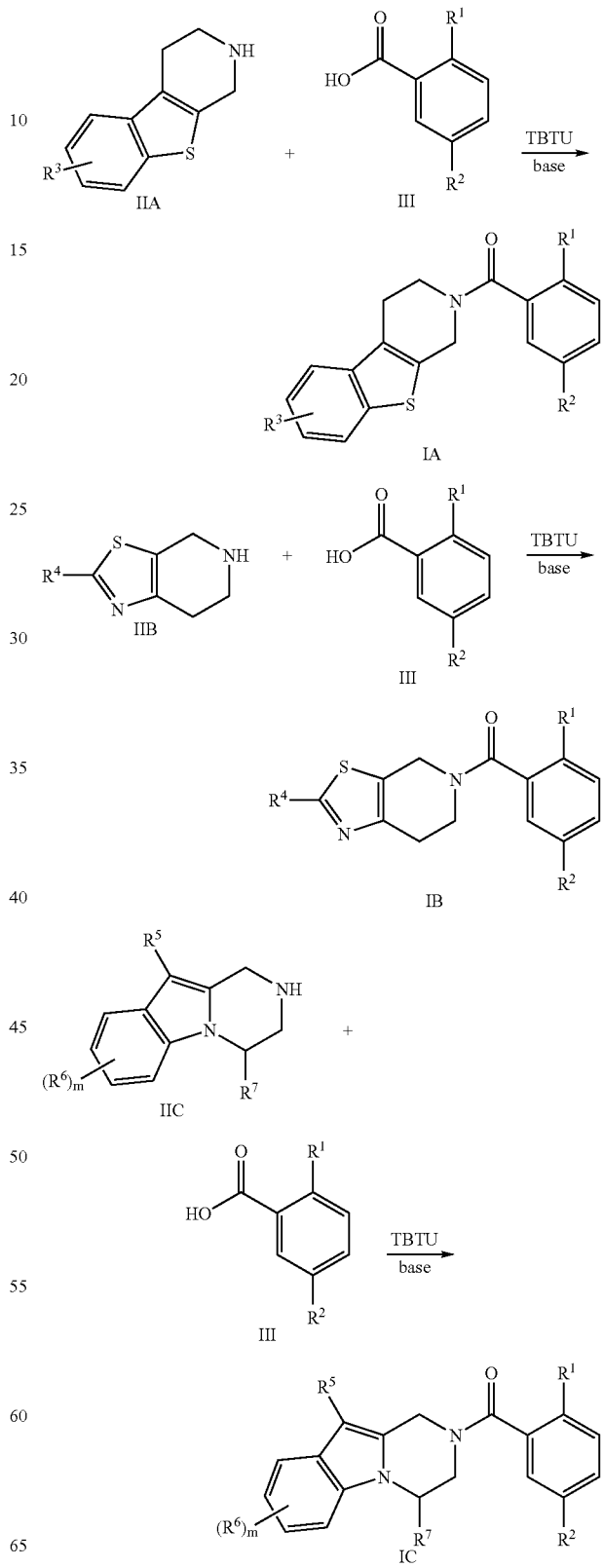

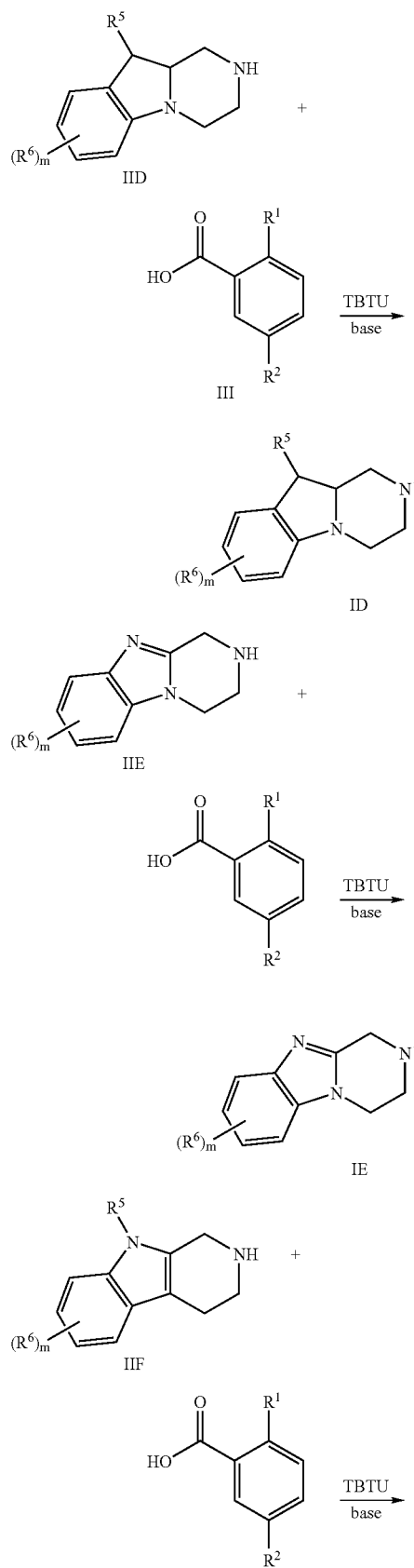

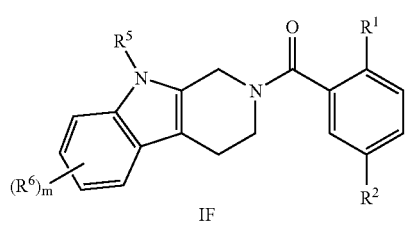

wherein $R^1$-$R^7$ are as described above.

A compound of formula II (IIA, IIB, IIC, IID, IIE or IIF) is treated with a compound of formula III in the presence of TBTU and a base, such as N-ethyldiisopropylamine to obtain a compound of formula I (IA, IB, IC, ID, IE or IF).

Scheme 2

Preparation of compounds of formula III:

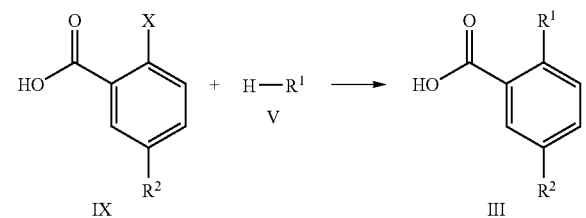

wherein $R^1$ and $R^2$ are as described above and X is halogen.

Compounds of formula III can be prepared in conventional manner. If H-$R^1$ is a non aromatic heterocycle, for example morpholine, the reaction is carried out at room temperature for about 2 hours.

If $R^1$ is OR' for R' is lower alkyl, lower alkyl, substituted by halogen or —(CH$_2$)$_n$-cycloalkyl, the reaction is carried out with the corresponding alcohol of formula V by reaction with a mixture of a compound of formula IX and Cu(I)Br in triethylamine.

Compounds of formula IX can be prepared in conventional manner, for example as follows: To a corresponding benzoic acid in methanol at 0° C. oxone® (potassium peroxymonosulfate 2KHSO$_5$.KHSO$_4$.K$_2$SO$_4$) was added and the mixture was allowed to stir at RT.

Scheme 3

Preparation of compounds of formula I:

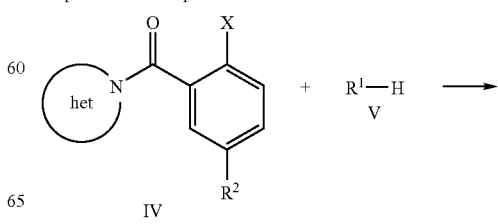

-continued

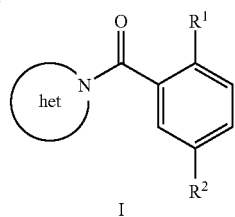

I wherein $R^1$, $R^2$ and

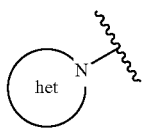

are as described above and X is halogen.

X can be replaced by $R^1$ in a conventional manner, for example with a base such as triethylamine or with Cu(I)Br.

Scheme 4

Preparation of compounds of formula I1:

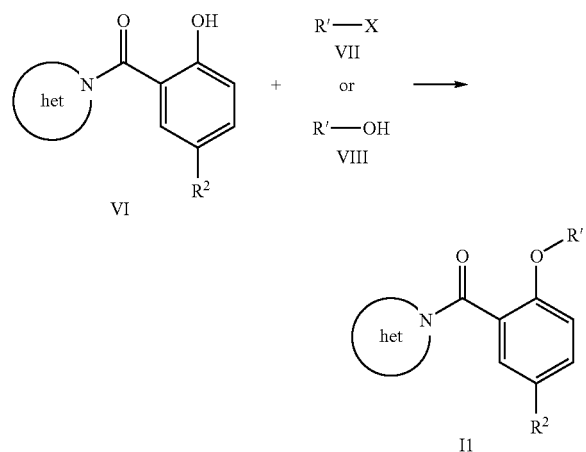

wherein R' and $R^2$ and

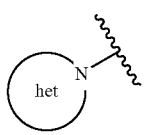

are as described above and X is halogen.

The acid addition salts of the basic compounds of formula I can be converted to the corresponding free bases by treatment with at least a stoichiometric equivalent of a suitable base such as sodium or potassium-hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

SOLUTIONS AND MATERIALS

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies).

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07)cells stably transfected with mGlyT1b cDNA.

Glycine uptake inhibition assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentration of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

Representative compounds show-an $IC_{50}$ (µM) at GlyT-1<0.5.

| Example No. | $IC_{50}$ (µM) |
| --- | --- |
| 1 formula IA | 0.019 |
| 2 formula IA | 0.187 |
| 5 formula IB | 0.098 |
| 6 formula IB | 0.407 |
| 9 formula IC | 0.134 |
| 11 formula IC | 0.088 |
| 14 formula ID | 0.154 |
| 15 formula IE | 0.367 |
| 19 formula IA | 0.339 |
| 20 formula A | 0.026 |
| 22 Example A | 0.023 |
| 23 Example B | 0.341 |

The present invention also provides pharmaceutical compositions containing compounds of the invention, for example, compounds of formula I or their pharmaceutically active acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or salts etc. can be used as such excipients e.g. for tablets, dragées, and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, if desired, one or more other therapeutically valuable substances into a galenical administration form together with one or more therapeutically inert carriers.

Compounds of the invention are inhibitors of the glycine transporter 1 (GlyT-1) and have good selectivity to glycine transporter 2 (GlyT-2) inhibitors. Therefore, these compounds are useful for the treatment of diseases related to activation of NMDA receptors via GlyT-1 inhibition. The present invention provides methods for treating neurological and neuropsychiatric disorders such as psychoses, dysfunction in memory and learning, schizophrenia, dementia and other diseases in which cognitive processes are impaired, such as attention deficit disorders or Alzheimer's disease.

The present invention provides a method of treating schizophrenia which comprises administering to an individual a therapeutically effective amount of a compound of formula I or a pharmaceutically acceptable salt thereof. The present invention also provides a method of treating cognitive impairment, which comprises administering to an individual a therapeutically effective amount of a compound of formula I or a pharmaceutically acceptable salt thereof. The present invention provides a method of treating Alzheimer's disease, which comprises administering to an individual a therapeutically effective amount of a compound of formula I or a pharmaceutically acceptable salt thereof.

The compounds and compositions of the present invention can be administered in a conventional manner, for example, orally, rectally, or parenterally. The compounds of the invention can be administered orally, for example, in the form of tablets, coated tablets, dragées, hard and soft gelatine capsules, solutions, emulsions, or suspensions. The compounds of the invention can be administered rectally, for example, in the form of suppositories or parenterally, for example, in the form of injectable solutions.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Hydrous Lactose | 1 | 59 | 123 | 148 |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. All temperatures are given in degree Celsius.

All starting materials are either commercially available, described in the literature or can be prepared by methods well known in the art.

EXAMPLE A

Preparation of 2-Morpholin-4-yl-5-nitro-benzoic acid

To a solution of 2-fluoro-5-nitrobenzoic acid (4.86 g, 26.2 mmol) in dioxane (50 ml) was added morpholine (11.5 mL). The mixture was stirred at room temperature for 2 hours. The solvent was removed in vacuo. The residue was dissolved in water, and the mixture was acidified with HCl 2N. The solid was filtered, washed with water and dried to provide the title compound (6.2 g, 93%) as a yellow solid, MS (m/e): 251.2 (MH$^-$, 100%).

EXAMPLE B

Preparation of
2-Isopropoxy-5-methanesulfonyl-benzoic acid

(a) 2-Chloro-5-methanesulfonyl-benzoic acid

To 99 mmol 2-chloro-5-(methylthio) benzoic acid in 400 ml methanol at 0° C. 296 mmol oxone® was added, and the mixture was allowed to stir at RT for 3.5 h. The precipitate was filtered off, and the filtrate was concentrated under reduced pressure. The residue was extracted 3× with 400 ml ethyl acetate and the combined organic phases washed 2× with 300 mL 1N HCl and with 300 mLl saturated aqueous NaCl solution and dried with $MgSO_4$. Evaporation under reduced pressure yielded the title compound.

(b) 2-Isopropoxy-5-methanesulfonyl-benzoic acid

A mixture of 2.13 mmol 2-chloro-5-methanesulfonyl-benzoic acid, 0.64 mmol Cu(I)Br in 5 mL $NEt_3$ and 25 mL isopropanol was heated to 120° C. for 16 h in a sealed tube. The volatiles were removed under vacuum, and the residue was taken up in 70 mL 1N HCl. Extraction with ethyl acetate drying of the combined organic fractions and evaporation yielded a residue which was purified by reversed phase preparative HPLC eluting with an acetonitrile/water gradient. Evaporation of the product fractions yielded the title compound 1.2.
MS (m/e): 257.0 (MH$^-$, 100%)

EXAMPLE C

Preparation of
2-Isobutoxy-5-methanesulfonyl-benzoic acid

Prepared in analogy to example B from 2-chloro-5-methanesulfonyl-benzoic acid and isobutanol.
MS (m/e): 271.1 (MH$^-$, 100%)

EXAMPLE D

5-Methanesulfonyl-2-morpholin-4-yl-benzoic acid

Prepared in analogy to example B from 2-chloro-5-methanesulfonyl-benzoic acid and morpholine. MS (m/e): 284.1 (MH$^-$, 100%).

EXAMPLE E

2-Thiophen-2-yl-4,5,6,7-tetrahydro-thiazolo[5,4-c]pyridine

(a) 1-(2-Thiophen-2-yl-6,7-dihydro-4H-thiazolo[5,4-c]pyridin-5-yl)-ethanone 2.8 mmol of thiophene-2-thiocarboxamide was dissolved in 10 ml acetonitrile. 5.6 mmol of N-ethyl-diisopropylamine was added, followed by 3.4 mmol 1-acetyl-3-bromo-piperidin-4-one hydrobromide (prepared according to patent U.S. Pat No. 4,122,083). The reaction mixture was heated to 50° C. for 4 hours, cooled and concentrated. Chromatography of the residue ($SiO_2$; ethyl acetate) yields the title compound as a yellowish gum. MS (m/e): 265.0 (M+H$^+$).

(b) 2-Thiophen-2-yl-4,5,6,7-tetrahydro-thiazolo[5,4-c]pyridine 1 mmol of 1-(2-Thiophen-2-yl-6,7-dihydro-4H-thiazolo [5,4-c]pyridin-5-yl)-ethanone was refluxed for 30 min. in 15 ml of 2 M aqueous hydrochloric acid. The reaction mixture was cooled and made alkaline by addition of sodium carbonate. Extraction with ethyl acetate yields the title compound as a brownish solid. MS (m/e): 223.3 (M+H$^+$).

EXAMPLE F 2-(4-Fluoro-phenyl)-4,5,6,7-tetrahydro-thiazolo[5,4-c]pyridine

(a) 1-[2-(4-Fluoro-phenyl)-6,7-dihydro-4H-thiazolo[5,4]pyridin-5-yl]-ethanone Prepared in analogy to example E (a) from 4-fluoro-1-benzenecarbothioamide and 1-acetyl-3-bromo-piperidin-4-one hydrobromide as a colorless solid. MS (m/e): 277.1 (M+H$^+$).

(b) 2-(4-Fluoro-phenyl)-4,5,6,7-tetrahydro-thiazolo[5,4-c]pyridine

Prepared in analogy to example E (b) from 1-[2-(4-fluoro-phenyl)-6,7-dihydro-4H-thiazolo[5,4]pyridin-5-yl]-ethanone and hydrochloric acid. Chromatography ($SiO_2$; dichloromethane/methanol 95:5) yields the title compound as a yellowish solid. MS (m/e): 235.1 (M+H$^+$).

EXAMPLE G

Preparation of
2-Cyclopentyloxy-5-methanesulfonyl-benzoic acid

Prepared in analogy to example B from 2-chloro-5-methanesulfonyl-benzoic acid and cyclopentanol, MS (m/e): 283.1 (MH$^-$, 100%).

EXAMPLE H

8-Trifluoromethoxy-1,2,3,4-tetrahydro-pyrazino[1,2-a]indole a) 1-Cyanomethyl-5-trifluoromethoxy-1H-indole-2-carboxylic acid ethyl ester

To a solution of sodium hydride (0.58 g in DMF (12 mL) at 0° C. was slowly added a solution of 5-trifluoromethoxy-1H-indole-2-carboxylic acid ethyl ester (2.64 g) in DMF (12 mL) keeping the temperature below 7.5° C. After gas evolution ceased, chloroacetonitrile was added, and the reaction mixture was stirred for 2 hours at 75° C. After allowing cooling down, water was added, and the reaction mixture was extracted with ethyl acetate. The combined organic phases were washed with brine then dried with magnesium sulfate, concentrated in vacuo and purified by column chromatography to yield the title compound (2.3 g, 76%). MS (EI): 312.1 (M$^+$).

b) 8-Trifluoromethoxy-1,2,3,4-tetrahydro-pyrazino[1,2-a]indole

To a suspension of Lithium Aluminium Hydride (0.68 g) in diethylether (70 mL) was added portionwise 1-cyanom ethyl-5-trifluoromethoxy-1H-indole-2-carboxylic acid ethyl ester (2.28 g). The reaction mixture was then stirred for 16 hours at reflux. The solution was then slowly poured into a saturated solution of sodium-potassium tartrate. The mixture was then extracted with ethyl acetate 3 times. The combined organic phases were then washed with brine, dried with magnesium sulfate, concentrated in vacuo and purified by column chromatography to yield the desired compound (0.83 g, 45%).

MS (EI): 274.0 (M+).

EXAMPLE I

Rac-8-Trifluoromethoxy-1,2,3,4,10,10a-hexahydro-pyrazino[1,2-a]indole

To 8-trifluoromethoxy-1,2,3,4-tetrahydro-pyrazino[1,2-a]indole (0.41 g) in THF (2.2 mL) and TFA (4.4 mL) at 0° C. was added portion wise sodium borohydride (0.124 g). The reaction mixture was allowed to warm up to room temperature and stirred for 35 minutes. After such time, the reaction mixture was concentrated in vacuo, and the residue was dissolved in dichloromethane and poured over water. A sodium hydroxide solution (10 M) was the added until reaching pH 13.5. After 15 minutes, the phases were separated. The aqueous phase was extracted with dichloromethane twice. The combined organic layers were then washed with brine, dried with magnesium sulfate, concentrated in vacuo and purified by column chromatography to yield the title compound (0.31 g, 76%).

MS (EI): 258.1 (M+).

EXAMPLE 1

(6-Chloro-3,4-dihydro-1H-benzo[4,5]thieno[2,3-c]pyridin-2-yl)-(2-isopropoxy-5-methanesulfonyl-phenyl)-methanone

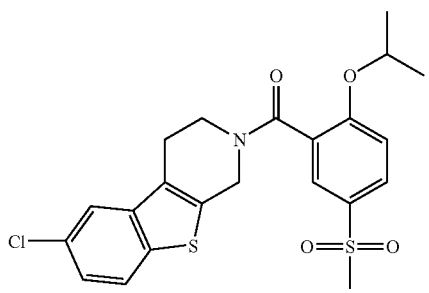

A solution of 2-isopropoxy-5-methanesulfonyl-benzoic (Example B, 30 mg), and 6-chloro-1,2,3,4-tetrahydro-benzo[4,5]thieno[2,3-c]pyridine ([29078-50-0], 35 mg), N-diisopropylethyalmine (0.12 m), and TBTU (2-(1H-benzotriazole-1-yl)-1,1,3,3-tetramethyluroniumtetrafluoroborate, 55 mg) in dimethylformamide (2 mL) was stirred at room temperature for 16 hours. The reaction mixture was concentrated and purified by column chromatography (SiO₂, Heptane/EtOAc 0-100%) to yield the title compound as a white solid (30 mg). MS (m/e): 464.1 (M+H+).

EXAMPLE 2

(6-Chloro-3,4-dihydro-1H-benzo[4,5]thieno[2,3-c]pyridin-2-yl)-(5-methanesulfonyl-2-morpholin-4-yl-phenyl)-methanone

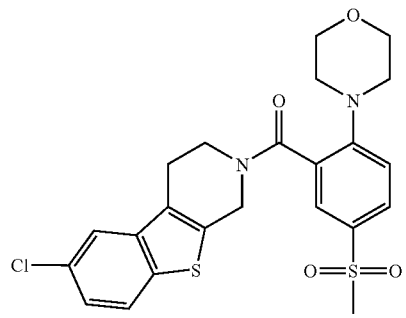

The title compound was prepared in analogy to Example 1 using Example D and 6-chloro-1,2,3,4-tetrahydro-benzo[4,5]thieno[2,3-c]pyridine [29078-50-0].

MS (m/e): 491.1 (M+H+).

EXAMPLE 3

(2-Isopropoxy-5-methanesulfonyl-phenyl)-[2-(4-trifluoromethyl-phenyl)-6,7-dihydro-4H-thiazolo[5,4-c]pyridin-5-yl]-methanone

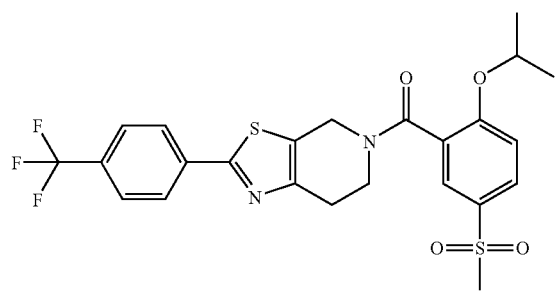

The title compound was prepared in analogy to Example 1 using Example B and 2-[4-(trifluoromethyl)phenyl]-4,5,6,7-tetrahydro[1,3]triazolo[5,4-c]pyridine[733757-96-5].

MS (m/e): 525.2 (M+H+).

EXAMPLE 4

(2-Morpholin-4-yl-5-nitro-phenyl)-(2-thiophen-2-yl-6,7-dihydro-4H-thiazolo[5,4-c]pyridin-5-yl)-methanone

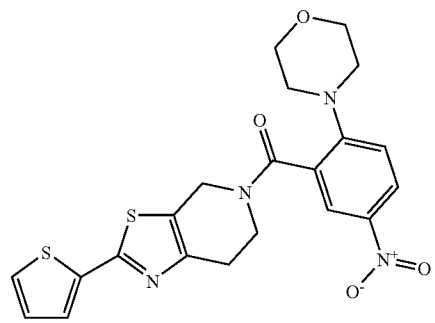

The title compound was prepared in analogy to Example 1 using Example A and Example E. MS (m/e): 457.3 (M+H+).

EXAMPLE 5

(2-Isobutoxy-5-methanesulfonyl-phenyl)-(2-thiophen-2-yl-6,7-dihydro-4H-thiazolo[5,4-c]pyridin-5-yl)-methanone

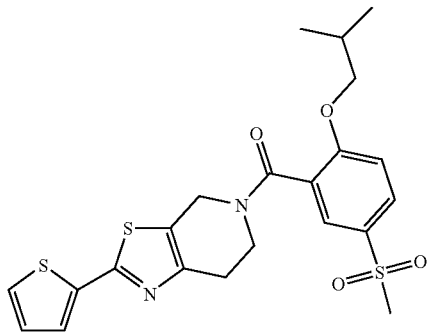

The title compound was prepared in analogy to Example 1 using Example C and Example E. MS (m/e): 477.0 (M+H$^+$).

EXAMPLE 6

(2-Isopropoxy-5-methanesulfonyl-phenyl)-(2-thiophen-2-yl-6,7-dihydro-4H!-thiazolo[5,4-c]pyridin-5-yl)-methanone

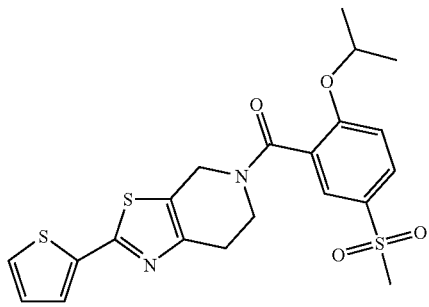

The title compound was prepared in analogy to Example 1 using Example B and Example E. MS (m/e): 463.3 (M+H$^+$).

EXAMPLE 7

(2-Ethyl-6,7-dihydro-4H-thiazolo[5,4-c]pyridin-5-yl)-(2-isopropoxy-5-methanesulfonyl-phenyl)-methanone

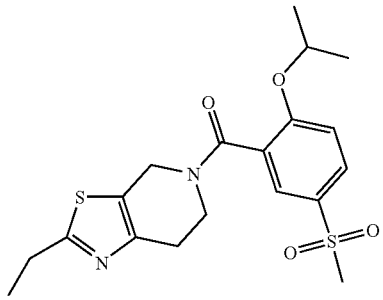

The title compound was prepared in analogy to Example 1 using Example B and 2-ethyl-4,5,6,7-tetrahydrothiazolo[5,4-c]pyridine [153341-59-4]. MS (m/e): 409.4 (M+H$^+$).

EXAMPLE 8

[2-(4-Fluoro-phenyl)-6,7-dihydro-4H-thiazolo[5,4-c]pyridin-5-yl]-(2-isobutoxy-5-methanesulfonyl-phenyl)-methanone

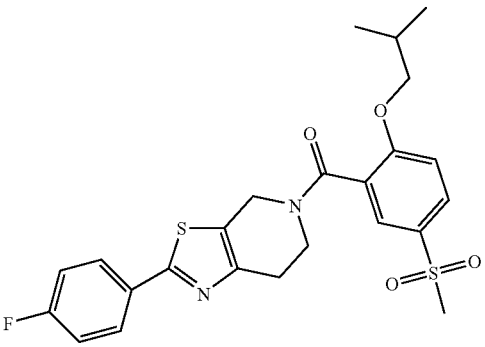

The title compound was prepared in analogy to Example 1 using Example C and Example F. MS (m/e): 489.0 (M+H$^+$).

EXAMPLE 9

(7-Chloro-3,4-dihydro-1H-pyrazino[1,2-a]indol-2-yl)-(2-isopropoxy-5-methanesulfonyl-phenyl)-methanone

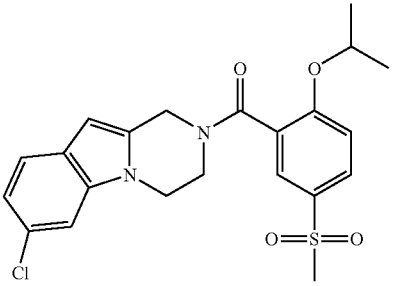

The title compound was prepared in analogy to Example 1 using Example B and 7-chloro-1,2,3,4-tetrahydro-pyrazino[1,2-a]indole [287384-61-6]. MS (m/e): 447.0 (M+H$^+$).

EXAMPLE 10

(9-Fluoro-10-methoxy-3,4-dihydro-1H-pyrazino[1,2-a]indol-2-yl)-(2-isopropoxy-5-methanesulfonyl-phenyl)-methanone

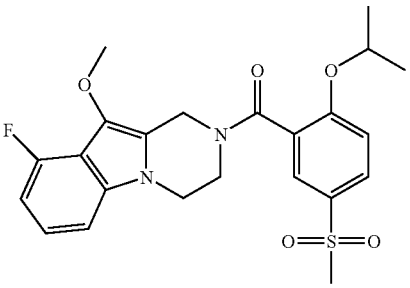

The tide compound was prepared in analogy to Example 1 using Example B and 9-fluoro-1,2,3,4-tetrahydro-10-methoxy-pyrazino[1,2-a]indole [153500-96-0]. MS (m/e): 478.1 (M+NH$_4^+$).

EXAMPLE 11

(2-Isopropoxy-5-methanesulfonyl-phenyl)-(8-trifluoromethoxy-3,4-dihydro-1H-pyrazino[1,2-a]indol-2-yl)-methanone

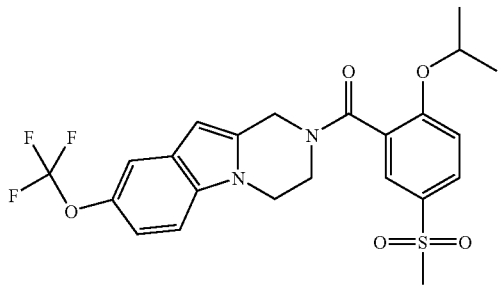

The title compound was prepared in analogy to Example 1 using Example B and Example H. MS (m/e): 497.1 (M+H⁺).

EXAMPLE 12

(2-Isopropoxy-5-methanesulfonyl-phenyl)-((R)-4-methyl-7-trifluoromethyl-3,4-dihydro-1H-pyrazino[1,2-a]indol-2-yl)-methanone

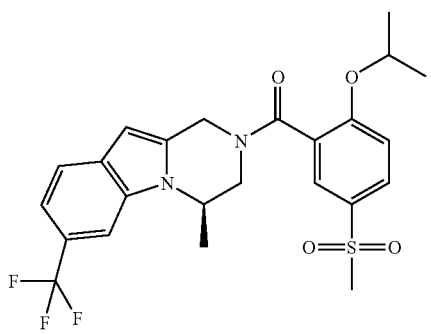

The title compound was prepared in analogy to Example 1 using Example B and (R)-4-methyl-7-trifluoromethyl-1,2,3,4-tetrahydropyrazino[1,2-a]indole [396074-54-7]. MS (m/e): 495.3 (M+H⁺).

EXAMPLE 13

((R)-7,9-Dichloro-4-methyl-3,4-dihydro-1H-pyrazino[1,2-a]indol-2-yl)-(2-isopropoxy-5-methanesulfonyl-phenyl)-methanone

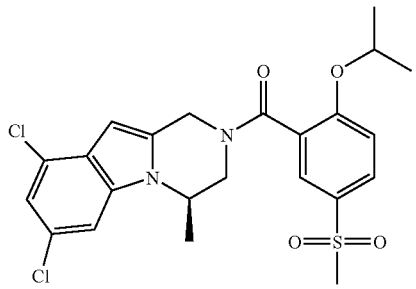

The title compound was prepared in analogy to Example 1 using Example B and (4R)-7,9-dichloro-1,2,3,4-tetrahydro-4-methyl-pyrazino[1,2-a]indole [763077-49-2]. MS (m/e): 495.4 (M+H⁺).

EXAMPLE 14

Rac-(2-Isopropoxy-5-methanesulfonyl-phenyl)-(8-trifluoromethoxy-3,4,10,10a-tetrahydro-1H-pyrazino[1,2-a]indol-2-yl)-methanone

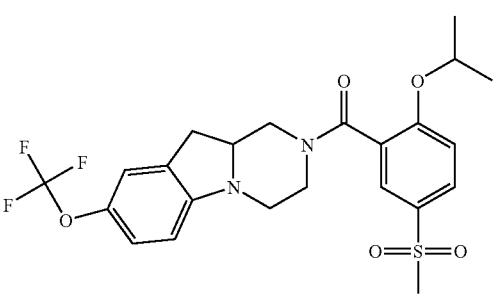

The title compound was prepared in analogy to Example 1 using Example B and Example I. MS (m/e): 499.1 (M+H⁺).

EXAMPLE 15

(2-Cyclopentyloxy-5-methanesulfonyl-phenyl)-(3,4-dihydro-1H-benzo[4,5]imidazo[1,2-a]pyrazin-2-yl)-methanone

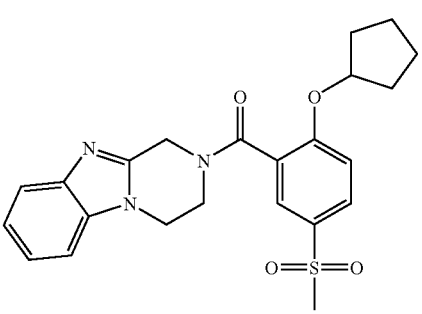

The title compound was prepared in analogy to Example 1 using Example G and 1,2,3,4-tetrahydropyrazino[1,2-a]benzimidazole [4744-53-0]. MS (m/e): 440.4 (M+H⁺).

EXAMPLE 16

(3,4-Dihydro-1H-benzo[4,5]imidazo[1,2-a]pyrazin-2-yl)-(2-isobutoxy-5-methanesulfonyl-phenyl)-methanone

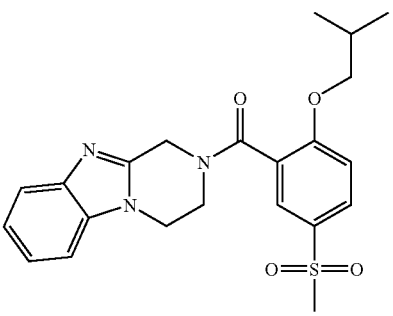

The title compound was prepared in analogy to Example 1 using Example C and 1,2,3,4-tetrahydropyrazino[1,2-a]benzimidazole [4744-53-0]. MS (m/e): 428.5 (M+H⁺).

EXAMPLE 17

(6-Fluoro-1,3,4,5-tetrahydro-pyrido[4,3-b]indol-2-yl)-(2-isopropoxy-5-methanesulfonyl-phenyl)-methanone

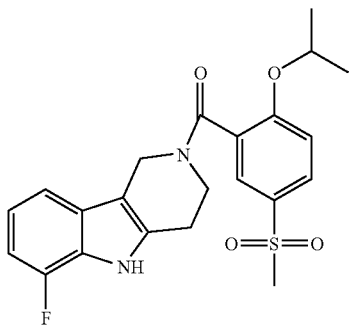

The title compound was prepared in analogy to Example 1 using Example B and 6-fluoro-2,3,4,5-tetrahydro-1H-pyrido{4,3-b}indole [177858-77-4]. MS (m/e): 431.1 (M+H⁺).

EXAMPLE 18

(6-Fluoro-5-methanesulfonyl-1,3,4,5-tetrahydro-pyrido[4,3-b]indol-2-yl)-(2-isopropoxy-5-methanesulfonyl-phenyl)-methanone

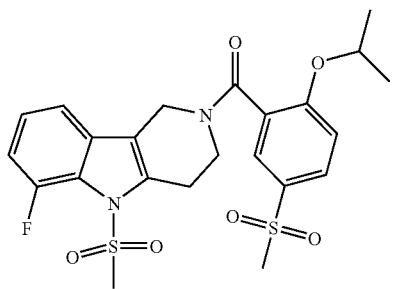

A suspension of 200 mg (6-fluoro-1,3,4,5-tetrahydro-pyrido[4,3-b]indol-2-yl)-(2-isopropoxy-5-methanesulfonyl-phenyl)-methanone (Example 17) in 5 ml dichloromethane was treated with 106 mg methane sulfonyl chloride, followed by 118 mg triethylamine. The reaction mixture was stirred overnight. Concentration and chromatography (silica gel; ethyl acetate) yielded the title compound as a slightly yellowish solid (17 mg; 7%). MS (m/e): 509.0 (M+CH₃COO).

EXAMPLE 19

3-(6-Chloro-3,4-dihydro-1H-benzo[4,5]thieno[2,3-c]pyridine-2-carbonyl)-4-isopropoxy-benzonitrile

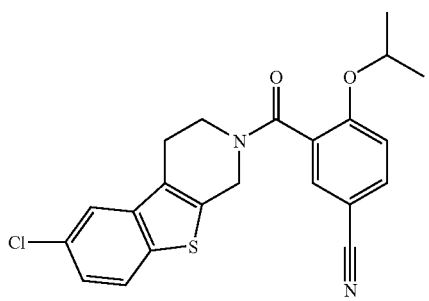

The title compound was prepared in analogy to Example 1 using 6-chloro-1,2,3,4-tetrahydro-[1]benzothieno[2,3-c]pyridine [29078-50-0] and 5-cyano-2-(1-methylethoxy)-benzoic acid[845616-14-0]. MS (m/e): 411.0 (M+H⁺).

EXAMPLE 20

(6-Chloro-3,4-dihydro-1H-benzo[4,5]thieno[2,3-c]pyridin-2-yl)-(2-cyclopropylmethoxy-5-methanesulfonyl-phenyl)-methanone

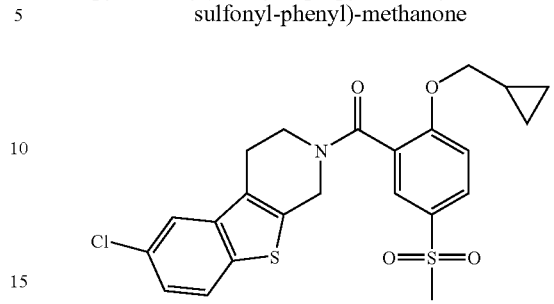

The title compound was prepared in analogy to Example 1 using 6-chloro-1,2,3,4-tetrahydro-[1]benzothieno[2,3-c]pyridine [29078-50-0] and 2-cyclopropylmethoxy-5-methylsulfonylbenzoic acid[845616-03-7]. MS (m/e): 476.0 (M+H⁺).

EXAMPLE 21

(6-Chloro-3,4-dihydro-1H-benzo[4,5]thieno[2,3-c]pyridin-2-yl)-(2-diethylamino-5-nitro-phenyl)-methanone

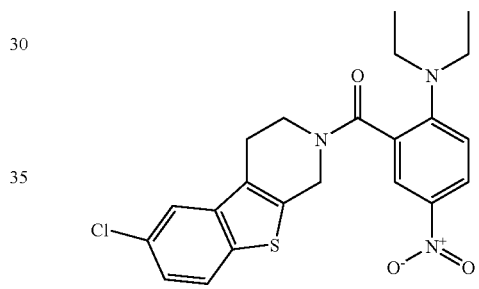

The title compound was prepared in analogy to Example 1 using 6-chloro-1,2,3,4-tetrahydro-[1]benzothieno[2,3-c]pyridine [29078-50-0] and 2-(diethylamino)-5-nitro-benzoic acid [727718-14-1]. MS (m/e): 444.1 (M+H⁺).

EXAMPLE 22

(6-Chloro-3,4-dihydro-1H-benzo[4,5]thieno[2,3-c]pyridin-2-yl)-[5-methanesulfonyl-2-((S)-2,2,2-trifluoro-1-methyl-ethoxy)-phenyl]-methanone

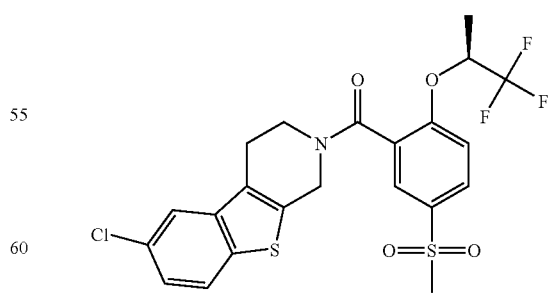

The title compound was prepared in analogy to Example 1 using 6-chloro-1,2,3,4-tetrahydro-[1]benzothieno[2,3-c]pyridine [29078-50-0] and 5-methylsulfonyl-2-[((S)-2,2,2-trifluoro-1-methylethyl)oxy]benzoic acid [845616-82-2]. MS (m/e): 518.1 (M+H⁺).

EXAMPLE 23

(2-Isobutoxy-5-methanesulfonyl-phenyl)-[2-(4-trifluoromethyl-phenyl)-6,7-dihydro-4H-thiazolo[5,4-c]pyridin-5-yl]-methanone

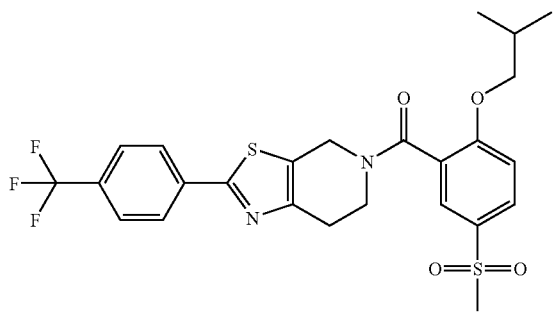

The title compound was prepared in analogy to Example 1 using 2-[4-(trifluoromethyl)phenyl]-4,5,6,7-tetrahydro[1,3]triazolo[5,4-c]pyridine [733757-96-5] and Example C. MS (m/e): 539.3 (M+H$^+$).

EXAMPLE 24

(3,4-Dihydro-1H-benzo[4,5]imidazo[1,2-a]pyrazin-2-yl)-(2-isopropoxy-5-methanesulfonyl-phenyl)-methanone

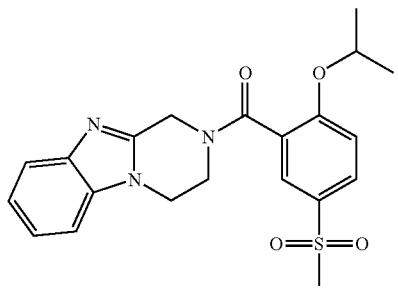

The title compound was prepared in analogy to Example 1 using 1,2,3,4-tetrahydropyrazino[1,2-a]benzimidazole [4744-53-0] and Example B. MS (m/e): 414.3 (M+H$^+$).

The invention claimed is:

1. A compound of formula IA

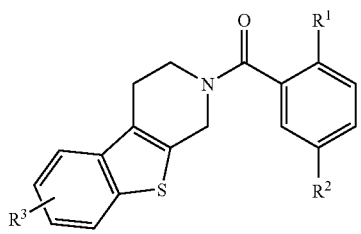

wherein
R$^1$ is a non aromatic heterocycle, OR' or N(R")$_2$;
R' is lower alkyl, lower alkyl substituted by halogen or —(CH$_2$)$_n$-cycloalkyl;
R" is lower alkyl;
R$^2$ is NO$_2$, CN or SO$_2$R";
R$^3$ is hydrogen, halogen, lower alkyl, lower alkoxy, or lower alkyl substituted by halogen;
n is 0, 1 or 2;
or a pharmaceutically active acid addition salt thereof.

2. A compound of claim 1, selected from the group consisting of
(6-Chloro-3,4-dihydro-1H-benzo[4,5]thieno[2,3-c]pyridin-2-yl)-(2-isopropoxy-5-methanesulfonyl-phenyl)-methanone,
(6-Chloro-3,4-dihydro-1H-benzo[4,5]thieno[2,3-c]pyridin-2-yl)-(5-methanesulfonyl-2-morpholin-4-yl-phenyl)-methanone,
3-(6-chloro-3,4-dihydro-1H-benzo[4,5]thieno[2,3-c]pyridine-2-carbonyl)-4-isopropoxy-benzonitrile,
(6-chloro-3,4-dihydro-1H-benzo[4,5]thieno [2,3-c]pyridin-2-yl)-(2-cyclopropylmethoxy-5-methanesulfonyl-phenyl)-methanone and
(6-chloro-3,4-dihydro-1H-benzo[4,5]thieno[2,3-c]pyridin-2-yl)-[5-methanesulfonyl-2-((S)-2,2,2-trifluoro-1-methyl-ethoxy)-phenyl]-methanone.

3. A pharmaceutical composition comprising a therapeutically effective amount of a compound of formula IA

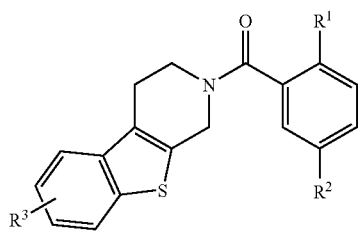

wherein
R$^1$ is a non aromatic heterocycle, OR' or N(R")$_2$;
R' is lower alkyl, lower alkyl substituted by halogen or —(CH$_2$)$_n$-cycloalkyl;
R" is lower alkyl;
R$^2$ is NO$_2$, CN or SO$_2$R";
R$^3$ is hydrogen, halogen, lower alkyl, lower alkoxy, or lower alkyl substituted by halogen;
n is 0, 1 or 2;
or a pharmaceutically active acid addition salt thereof and a pharmaceutically acceptable carrier.

4. A process for preparing a compound of formula IA

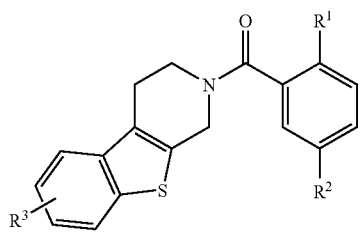

wherein
R$^1$ is a non aromatic heterocycle, OR' or N(R")$_2$;
R' is lower alkyl, lower alkyl substituted by halogen or —(CH$_2$)$_n$-cycloalkyl;
R" is lower alkyl;
R$^2$ is NO$_2$, CN or SO$_2$R";
R$^3$ is hydrogen, halogen, lower alkyl, lower alkoxy, or lower alkyl substituted by halogen;
n is 0, 1 or 2;
wherein the process is selected from the group consisting of a) reacting a compound of formula

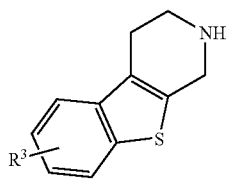

with a compound of formula

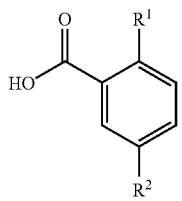

in the presence of an activating agent to produce a compound of formula

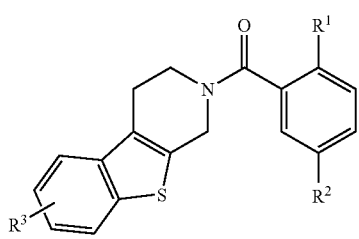  IA b) reacting a compound of formula

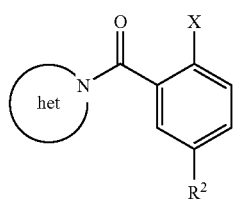  IV wherein

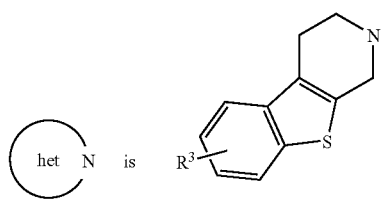

X is halogen;
with a compound of formula

R¹H  V in the presence of a base or a catalyst to produce a compound of formula

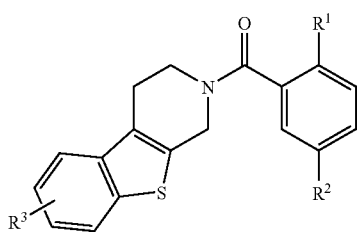  IIA

III c) reacting a compound of formula

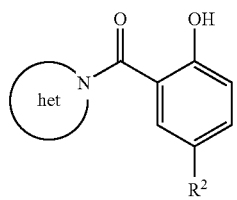  VI wherein

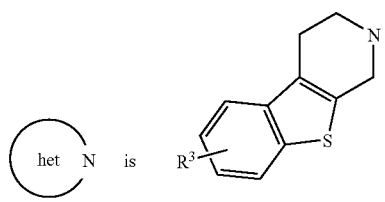 is with a compound of formula

R'X  VII to produce a compound of formula

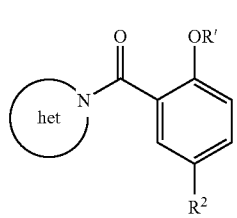  II wherein

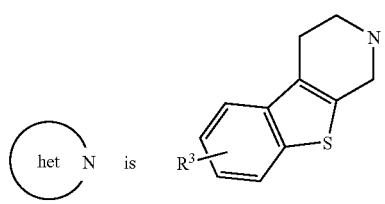 is

X is halogen; and d) reacting a compound of formula

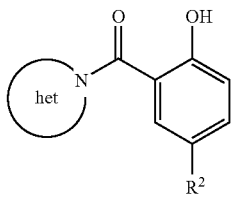

wherein

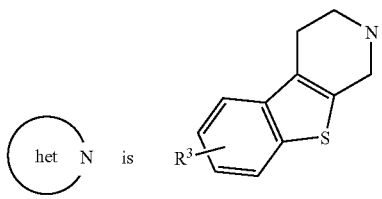

with a compound of formula

R'OH under Mitsunobu conditions to produce a compound of formula

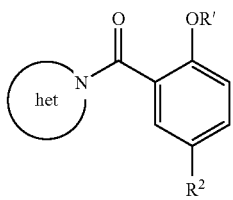

wherein

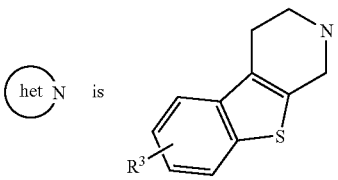      VI

5. A method of treating a disease selected from the group consisting of schizophrenia, cognitive impairment, and Alzheimer's disease comprising administering to an individual a therapeutically effective amount of a compound of formula I

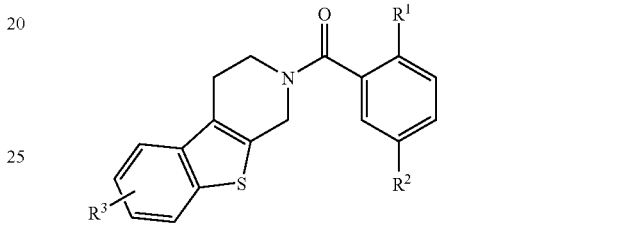   IA wherein
R' is a non aromatic heterocycle, OR' or N(R")$_2$;
R' is lower alkyl, lower alkyl substituted by halogen or —(CH$_2$)$_n$-cycloalkyl;
R" is lower alkyl;
R$^2$ is NO$_2$, CN or SO$_2$R"; R$^3$ is hydrogen, halogen, lower alkyl, lower alkoxy, or lower alkyl substituted by halogen;
n is 0, 1 or 2;
or a pharmaceutically active acid addition salt thereof.

6. A method of claim 5, wherein the disease is schizophrenia.

7. The method of claim 5, wherein the disease is cognitive impairment.

8. The method of claim 5, wherein the disease is Alzheimer's disease.

* * * * *